(12) United States Patent
White et al.

(10) Patent No.: US 11,666,606 B2
(45) Date of Patent: *Jun. 6, 2023

(54) METHODS OF TREATING JOINT DISEASE, DISORDERS AND CONDITIONS WITH TISSUE INHIBITORS OF MATRIX METALLOPROTEINASES

(71) Applicant: Prime Merger Sub, LLC, Birmingham, AL (US)

(72) Inventors: Jeffrey S. White, Birchrunville, PA (US); Robin R. Young, Beaverton, OR (US)

(73) Assignee: Prime Merger Sub, LLC, Birmingham, AL (US)

( * ) Notice: Subject to any disclaimer, the term of this patent is extended or adjusted under 35 U.S.C. 154(b) by 380 days.

This patent is subject to a terminal disclaimer.

(21) Appl. No.: 16/746,541

(22) Filed: Jan. 17, 2020

(65) Prior Publication Data

US 2020/0147144 A1 May 14, 2020

Related U.S. Application Data

(63) Continuation of application No. 15/086,985, filed on Mar. 31, 2016, now Pat. No. 10,576,107.

(60) Provisional application No. 62/140,909, filed on Mar. 31, 2015.

(51) Int. Cl.
| | |
|---|---|
| *A61K 35/50* | (2015.01) |
| *A61K 38/57* | (2006.01) |
| *A61L 27/54* | (2006.01) |
| *A61L 27/36* | (2006.01) |
| *A61K 9/00* | (2006.01) |
| *A61K 47/36* | (2006.01) |

(52) U.S. Cl.
CPC .............. *A61K 35/50* (2013.01); *A61K 38/57* (2013.01); *A61L 27/3604* (2013.01); *A61L 27/54* (2013.01); *A61K 9/0019* (2013.01); *A61K 47/36* (2013.01); *A61L 2300/434* (2013.01); *A61L 2430/24* (2013.01)

(58) Field of Classification Search
None
See application file for complete search history.

(56) References Cited

U.S. PATENT DOCUMENTS 5,643,752 A * 7/1997 Hawkins ............ C07K 14/8146
435/320.1

OTHER PUBLICATIONS

Shimberg, J. Bone Joint Surg. 20(1): 167-177 (1938).*
Bhattacharya, "Clinical Use of Amniotic Fluid in Osteoarthritis: A Source of Cell Therapy", p. 395-403, Regenerative Medicine Using Pregnancy-Specific Biological Substances, Springer Verlag London, 2011.*
Riley et al., J. Endocrinol. 162: 351-359 (1999).*
Bunning et al., Eur. J. Biochem. 139: 75-80 (1984).*

* cited by examiner

*Primary Examiner* — Erin M. Bowers
(74) *Attorney, Agent, or Firm* — C. Brandon Browning; Ilya S. Mirov; Maynard Nexsen PC

(57) ABSTRACT

Methods for treating joint diseases, disorders, and conditions, such as osteoarthritis, with a composition containing a therapeutically effective amount of tissue inhibitors of matrix metalloproteinases (TIMPs) are provided. The composition can contain TIMPs as part of amniotic fluid, or the TIMPs can be isolated from another source or recombinantly produced. The methods are particularly useful for treating osteoarthritis associated with degradation of articular cartilage by proteases. Also provided are methods of lubricating a joint, such as an osteoarthritic joint.

20 Claims, No Drawings

METHODS OF TREATING JOINT DISEASE, DISORDERS AND CONDITIONS WITH TISSUE INHIBITORS OF MATRIX METALLOPROTEINASES

CROSS REFERENCE TO RELATED APPLICATION

This application is a continuation application of U.S. application Ser. No. 15/086,985, filed Mar. 31, 2016, which is currently pending. U.S. application Ser. No. 15/086,985 claims the benefit of and priority to U.S. provisional application 62/140,909, filed on Mar. 31, 2015.

BACKGROUND OF THE INVENTION

Viscosupplements are viscous substances that can function as a lubricant and shock absorber for joints, and are often used to treat conditions of the human musculoskeletal system. Many viscosupplements typically used for treating inflammatory conditions of the human musculoskeletal system are produced via bacterial culturing, or by a process of extraction from tissues of a different species, such as rooster combs, which is the fleshy growth on top of the rooster's head.

The primary viscous, protecting, nutritional and lubricating fluid of the human musculoskeletal system responsible for maintaining healthy, articulating joints is synovial fluid. Synovial fluid is secreted by the synovial membrane, which is the soft tissue found between the articular capsule (joint capsule) and joint cavity. In native joints, synovial fluid functions as a biomechanical lubricant, lowering the friction and wear of articulating cartilage in joints. Synovial fluid lubricating macromolecules, including hyaluronic acid and proteoglycan 4 (PRG4), are secreted by synoviocytes in the synovial membrane lining the joint and chondrocytes in the cartilage of the joint, and are concentrated in synovial fluid due to the retaining property of the semi-permeable synovial membrane.

Currently available viscosupplements for the treatment of inflammatory conditions of the human musculoskeletal system are comprised of essentially a single component, hyaluronic acid (HA). Considering the complexity of naturally occurring synovial fluid, and the complex biological system necessary for maintaining the health and proper functioning of articulating joints, pure HA is not an ideal treatment for joints at least for physiological reasons.

Furthermore, the clinical record of currently available HA based viscosupplements is poor. That record was recently reviewed by the American Academy of Orthopedic Surgeons (AAOS), and in June 2013, the AAOS issued clinical practice guidelines to physicians, which recommended against using HA for patients with symptomatic osteoarthritis (OA) of the knee based on supporting evidence from several high-quality research studies that met the inclusion criteria.

The AAOS's clinical practice guidelines are based on some of the best peer reviewed study evidence available. According to the AAOS's website, currently published studies do not show a clinically effective response for HA injections based on minimal clinically important improvements (MCIIs). Some peer reviewers were critical of the AAOS' findings and recommendation, especially in light of the important clinical practice implications, and highlighted prior systematic reviews supporting the use of HA. However, these reviews were analyzed and found to have several flaws. For example, most did not address the issues of publication bias, between-study heterogeneity, and clinical significance in determining final recommendations.

Inflammation of articulating surfaces of the musculoskeletal system is one of the most common medical complaints. Although the exact causes for painful knee, hip, shoulder, facet, ankle, and wrist joints may be difficult to ascertain and in many cases are unknown, it is understood that degenerative damage, especially cartilage damage, plays a central role in the pathogenic mechanism leading to this disorder. Current treatment modalities include pharmacological treatments, physiotherapy, viscosupplement injections, corticosteroid injections and, at the terminus of a continuum of care for joint pain, surgical replacement of the joint. According to the Centers for Disease Control (CDC), nearly one in two people are projected to develop symptomatic knee osteoarthritis by age 85 years; two in three people who are obese are projected to develop symptomatic knee osteoarthritis in their lifetime; and one in four people are projected to develop hip arthritis in their lifetime. Also, according to the CDC, an estimated 52.5 million adults in the United Stated reported being told by a doctor that they have some form of arthritis, rheumatoid arthritis, gout, lupus, or fibromyalgia.

Moreover, by 2030, the number of Americans aged 18 years or older who are projected to have doctor-diagnosed arthritis is 67 million.

Present pharmacological treatments for such joint inflammation include the use of non-steroidal anti-inflammatory drugs (NSAIDs), such as naproxen, ibuprofen, etc., and drugs of the cyclooxygenase-2 inhibitor group like celecoxib, as well as other drugs including glucosamine, chondroitin, and opiates. Present non-pharmacological treatments include hot or cold packs around the inflamed joint; anaerobic exercises, such as resistance training; suggestion of weight loss or use of a crutch; use of a brace, particularly for the patella; and correction of joint tiling or misalignment.

However, many of the pharmacological and non-pharmacological treatments employed for treating joint inflammation suffer from several drawbacks. For example, corticosteroid injections are one of the most common anti-inflammatory treatments for joint pain, and it carries many risks including deteriorating articulating cartilage in the joint if overused, atrophy of subcutaneous fat, and nerve inflammation. There is, as a result, growing interest in the development of novel technologies to repair or regenerate the painful, degenerated articulating musculoskeletal bone and cartilage system.

Accordingly, there exists a need in the art for improved methods and compositions for treating inflammation of the human musculoskeletal system, and particularly of joint diseases, disorders, and conditions, such as osteoarthritis. Preferably, such improved methods and compositions provide the requisite lubrication, cushioning, and protection of the joint, but more closely resemble the composition of synovial fluid found in healthy articulating joints as compared to known viscosupplements.

BRIEF SUMMARY OF THE INVENTION

The invention satisfies this need by providing methods of treating joint disease, disorders, and conditions with a composition comprising a human amniotic fluid comprising a therapeutically effective amount of tissue inhibitors of matrix metalloproteinase, which can inhibit protease activity that contributes to cartilage degradation and degeneration in the joint, thus facilitating treatment of the joint disease, disorder, or condition.

In one general aspect, the invention relates to methods of treating joint diseases, disorders, and conditions with compositions comprising an amniotic fluid comprising a therapeutically effective amount of tissue inhibitors of matrix metalloproteinase.

In one embodiment, a method of treating a joint disease, disorder, or condition in a subject comprises injecting a composition comprising an amniotic fluid comprising a therapeutically effective amount of tissue inhibitors of matrix metalloproteinase (TIMPs) into the joint of the subject, thereby treating the joint disease, disorder, or condition.

In a preferred embodiment, the joint is a synovial joint.

In another embodiment, the joint disease, disorder, or condition is osteoarthritis, such as osteoarthritis associated with degradation of articular cartilage by proteases.

In particular embodiments of the invention, the amniotic fluid is processed by removing water to enrich the amniotic fluid for endogenous TIMPs.

In other particular embodiments of the invention, the amniotic fluid is obtained from a donor during a period of gestation when natural levels of TIMPs in the amniotic fluid are relatively high, such as between week 28 and week 37 of gestation.

In another general aspect, the invention provides a method of lubricating an osteoarthritic joint in a subject, wherein the osteoarthritis of the joint is associated with degradation of articular cartilage by proteases, the method comprising injecting into the joint a composition comprising an amniotic fluid comprising a therapeutically effective amount of tissue inhibitors of matrix metalloproteinases, thereby lubricating the osteoarthritic joint.

In another general aspect, the invention provides a method of treating a joint disease, disorder, or condition in a subject, the method comprising injecting a composition comprising a therapeutically effective amount of tissue inhibitors of matrix metalloproteinases (TIMPs) into the joint of the subject, thereby treating the joint disease, disorder, or condition.

In yet another general aspect, the invention provides a composition comprising an amniotic fluid comprising a therapeutically effective amount of tissue inhibitors of matrix metalloproteinases (TIMPs), wherein at least a portion of the TIMPs are exogenously added. The exogenous TIMPs can be recombinantly produced and/or isolated or purified from a natural source.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

It is now discovered that compositions comprising human amniotic fluid comprising a therapeutically effective amount of tissue inhibitors of matrix metalloproteinases are effective in treating joint diseases, disorders, and conditions, such as osteoarthritis, and particularly osteoarthritis associated with degradation of articular cartilage by proteases. Such compositions are also useful for lubricating an osteoarthritic joint to provide, for example, pain free joint movement.

As used herein, the term "subject" means any animal, and preferably a mammal. Examples of mammals include, but are not limited to, cows, horses, sheep, pigs, cats, dogs, mice, rats, rabbits, guinea pigs, monkeys, humans etc., more preferably a human.

As used herein, the term "donor" refers to a female subject from whom amniotic fluid will be or has been obtained. The donor can be any animal, preferably a mammal, e.g., bovine, human, or porcine, and is most preferably a human.

"Synovial fluid," as used herein, refers to the viscous fluid found in the cavities of synovial joints. Synovial fluid is also referred to as "joint fluid." Synovial fluid is secreted by the synovial membrane, which is the inner membrane lining a synovial joint. The primary role of synovial fluid is to reduce friction between articular cartilage of synovial joints during movement. Synovial fluid has other functions, including, but not limited to, reducing joint friction through lubrication, shock absorption, and nutrient and waste transportation.

As used herein, the term "joint disease, disorder, or condition" refers to any disease, disorder, or condition characterized by joint inflammation, cartilage inflammation in a joint, and/or cartilage degradation in a joint. Examples of joint diseases, disorders, or conditions include, but are not limited to, joint inflammation, such as arthritis, particularly osteoarthritis and rheumatoid arthritis; and inflammation of the cartilage, such as chondromalacia patellae.

Examples of joints include synovial joints, cartilaginous joints, and fibrous joints. According to embodiments of the invention, joint diseases, disorders, and conditions can affect synovial and/or cartilaginous joints. "Synovial joints" refer to the most common and movable type of joint in the body of a mammal. Synovial joints include hinge joints (e.g., elbow and knee), pivot joints (e.g., atlas and axis bones at the top of the neck), ball and socket joints (e.g., hip), saddle joints (e.g., carpometacarpal joint of the thumb), condyloid joints (e.g., wrist, metacarpophalangeal joints, metatarsophalangeal joint), and gliding joints (e.g., intercarpal joints in the wrist). "Cartilaginous joints" are joints connected entirely by cartilage, such as the manubrio-sternal joint (sternum) and amphiarthoses joints, such as intervertebral discs.

In certain embodiments of the invention, the joint disease, disorder, or condition to be treated affects a synovial joint. In other embodiments of the invention, the joint disease, disorder, or condition to be treated affects a cartilagnious joint.

Non-limiting examples of synovial joints include, but are not limited to, knee, wrist, shoulder, hip, elbow, facet, carpal-metacarpal, and tarsal/metatarsal joints.

In a preferred embodiment of the invention, the joint disease, disorder, or condition to be treated is osteoarthritis. As used herein, "osteoarthritis" refers to a form of arthritis occurring in synovial joints. It is usually a chronic condition, and occurs when the protective cartilage, known as articular cartilage, on the ends of bones that come together to form joints wears down and/or is degraded. "Articular cartilage" refers to the tissue at the ends of bones in joints, which provides frictionless contact between the bones in a joint during movement. Articular cartilage is composed of two major components: collagen and proteoglycans. The breakdown of cartilage in synovial joints can be caused by a number of factors including, but not limited to, proteases, aging, being overweight, and genetic defects in cartilage formation. Proteases known to cause degradation of cartilage include, but are not limited to, matrixmetalloproteinases.

In a particularly preferred embodiment of the invention, the joint disease, disorder, or condition to be treated is osteoarthritis associated with degradation of articular cartilage by proteases. As used herein, "osteoarthritis associated with degradation of articular cartilage by proteases" is intended to specifically refer to osteoarthritis, wherein protease degradation of articular cartilage causes, exacerbates, or contributes to the onset of the osteoarthritis. Proteases that cause, exacerbate, or contribute to the onset of the osteoarthritis include matrix metalloproteinases, and more particularly matrix metalloproteinases that degrade collagen.

The terms "matrix metalloproteinases" and "MMPs" are intended to refer to a family of zinc-dependent endopeptidases. MMPs play a role in many biological processes, including degradation of articular cartilage. MMPs are first produced and released in an inactive form known as the "pro-MMP" form. Inactive pro-MMPs are subsequently activated by proteases that cleave off a portion of the protein. Examples of MMPs include, but are not limited to, MMP-1, MMP-2, MMP-3, MMP-4, MMP-5, MMP-6, MMP-7, MMP-8, and MMP-9. Although the specific natural substrates for each of the MMPs varies, MMPs are generally capable of degrading extracellular matrix proteins, such as collagen, gelatin, proteoglycans, etc. The MMPs that are currently known to specifically play a role in cartilage extracellular matrix degradation include, but are not limited to, the collagenases (MMP-1, MMP-8, MMP-13), the stromelysins (MMP-3, MMP-10, MMP-11), the gelatinases (MMP-2, MMP-9), matrilysin (MMP-7), and membrane type MMPs, in particular MMP-14, which can also act as a collagenase.

As used herein, the terms "tissue inhibitor of matrix metalloproteinases" and "TIMPs" refer to a family of protease inhibitors that modulate the activity of matrix metalloproteinases. To date, it is known that the human genome encodes four TIMPs: TIMPI, TIMP2, TIMP3, and TIMP4. TIMPs modulate matrix metalloproteinases by inhibiting the activity of activated MMPs, or by blocking the activation of pro-MMPs. According to embodiments of the invention, an amniotic fluid comprising a therapeutically effective amount of TIMPs can affect the activity of MMPs in a joint by inhibiting the activity of activated MMPs, or by blocking the activation of pro-MMPs, thereby reducing the breakdown of cartilage by MMPs in the joint.

As used herein, the terms "treat," "treating," and "treatment" are all intended to refer to an amelioration or reversal of at least one measurable physical parameter related to a joint disease, disorder, or condition, which is not necessarily discernible in the subject, but can be discernible in the subject. The terms "treat," "treating," and "treatment," can also refer to preventing the progression, or at least slowing down the progression of the joint disease, disorder, or condition. In one embodiment, "treat," "treating," and "treatment" refer to a reduction or complete alleviation of pain associated with the joint disease, disorder, or condition. In another embodiment, "treat," "treating," and "treatment" refer to a reduction of joint inflammation. In yet another embodiment, "treat," "treating," and "treatment" refer to inhibiting or reducing the degradation of cartilage in a joint, such as articular cartilage in a synovial joint. And in yet another embodiment, "treat," "treating," and "treatment" refer to an alleviation of one or more symptoms associated with the joint disease, disorder, or condition, such as joint pain, joint swelling, joint stiffness, inflammation, difficulty in joint movement, and reduced range of motion.

The invention provides methods of treating joint diseases, disorders, and conditions in a subject.

In one general aspect, the invention provides a method of treating joint diseases, disorders, and conditions in a subject, the method comprising injecting into the joint a composition comprising an amniotic fluid comprising a therapeutically effective amount of tissue inhibitors of matrix metalloproteinases (TIMPs). TIMPs can inhibit the activity of proteases that increase cartilage degradation in a joint, particularly MMPs, thereby facilitating treatment of the joint disease, disorder, or condition.

According to embodiments of the invention, an amniotic fluid can be any amniotic fluid from a mammal including, but not limited to, bovine amniotic fluid, porcine amniotic fluid, and human amniotic fluid, and is most preferably human amniotic fluid.

Amniotic fluid naturally contains TIMPs, as well as many other regenerative components that are efficacious for treating joint diseases, disorders, and conditions, such as growth factors, stem cells, protease inhibitors, etc. Moreover, certain compositions used with the invention contain many of the same components as the synovial fluid found in healthy joints, and are thus particularly suited for covering, lubricated, protecting, and relieving joint inflammation and joint pain when injected into the joint. Accordingly, an advantage of providing a therapeutically effective amount of TIMPs in an amniotic fluid is that the other components naturally present in the amniotic fluid can further enhance treatment of joint diseases, disorders, and conditions, and further alleviate the symptoms thereof.

According to embodiments of the invention, the amniotic fluid of the composition comprises a therapeutically effective amount of tissue inhibitors of matrix metalloproteinases. The term "therapeutically effective amount" refers to an amount of an active ingredient or component that elicits the desired biological or medicinal response in a subject. As used herein with reference to tissue inhibitors of matrix metalloproteinases (TIMPs), a therapeutically effective amount means an amount of TIMPs that results in treatment of a joint disease, disorder, or condition; prevents or slows the progression of the joint disease, disorder, or condition; reduces or completely alleviates pain associated with the joint disease, disorder, or condition; reduces or prevents collagen degradation by proteases in the joint; reduces joint inflammation; or alleviates one or more symptoms associated with the joint disease, disorder, or condition, such as joint pain, joint swelling, joint stiffness, inflammation, reduced range of motion, and difficulty in joint movement.

One of ordinary skill in the art will recognize that the therapeutically effective amount of TIMPs to he used in the invention can vary with many factors, such as the particular subject, (e.g., age, diet, health, etc.); particular joint disease, disorder, or condition; severity of the joint disease, disorder, or condition; and any underlying complications or conditions in the subject that may have caused or contributed to the onset of the joint disease, disorder, or condition. For example, many osteoarthritis patients have one or more underlying complications or conditions that contribute to the onset and progression of osteoarthritis, such as obesity, etc.

According to embodiments of the invention, a therapeutically effective amount of TIMPs in the amniotic fluid can be provided by the natural level of TIMPs endogenously present in the amniotic fluid. Thus, an amniotic fluid collected from a donor can be used in a composition for injection into a joint without further processing or manipulation. In certain embodiments of the invention, the amniotic fluid is collected from the donor at a point during gestation when TIMP levels are typically elevated.

During gestation of an embryo, the body creates a placental sac made of amnion and chorion tissues surrounding the fetus and containing amniotic fluid to both protect and nourish the fetus. A purpose of TIMPs in amniotic fluid is to prevent the amnion and chorion tissues from being prematurely degraded by proteases, as such degradation would cause premature rupture of the placental sac and pre-term birth of the fetus. However, once the pregnancy has reached full term, TIMP levels in the amniotic fluid typically abruptly decrease, which allows for degradation of the amnion and chorion tissues, release of the amniotic fluid, and subsequent birth of the fetus. Thus, TIMP levels in amniotic fluid are usually at their highest during the late pre-term period of pregnancy, which prevents degradation of the amnion and chorion tissues, thus maintaining the integrity of the placental sac.

According to embodiments of the invention, the amniotic fluid, such as human amniotic fluid, can be obtained from a donor during gestation at a point when TIMP levels are typically near or at their maximum. As known by one of ordinary skill in the art, the gestation period in human females is divided into three trimesters: the first trimester (weeks one through twelve), the second trimester (weeks thirteen through twenty-seven), and the third trimester (weeks twenty-eight to birth). Gestation in human females is also characterized according to terms, i.e., specific periods of gestation during which birth occurs: pre-term (before 37 weeks of gestation), early term (37 weeks to 38 weeks, 6 days of gestation), full term (39 weeks to 40 weeks, 6 days of gestation), and late term (41 weeks to 41 weeks 6 days of gestation). TIMP levels have been demonstrated to fall rapidly in amniotic fluid at birth. Therefore, in a preferred embodiment, the amniotic fluid is obtained from a human donor at a point just prior to birth.

According to embodiments of the invention, human amniotic fluid for use in the invention can be obtained from a human female donor. Preferably, the human amniotic fluid is obtained at the time of Caesarean section delivery. When the Caesarean section delivery is elective, collection of the amniotic fluid can occur during the late pre-term period of pregnancy, i.e., during weeks 28 to 37 of gestation, and preferably closer to week 37 of gestation, when TIMP levels are typically at or near their maximum. For example, the amniotic fluid can be obtained during week 28, 29, 30, 31, 32, 33, 34, 35, 36, or 37 of gestation.

In a particularly preferred embodiment, amniotic fluid is obtained from a female donor undergoing a Caesarean section procedure, wherein the Caesarean section procedure takes place at a point during gestation near full term. Amniotic fluid obtained from a Caesarean section donor near term typically has a high concentration of TIMPs. As used herein, the phrase "near full term" refers to weeks 33-37 of gestation, such as week 33, 34, 35, 36, or 37 of gestation.

According to embodiments of the invention, the concentration of TIMPs in the amniotic fluid can be determined by testing a sample of amniotic fluid obtained at the time of Caesarean section, or by testing a sample previously obtained via amniocentesis, if desired. Any method known in the art in view of the present disclosure can be used to determine the concentration of TIMPs, such enzyme-linked immunoabsorbent assay (ELISA), Bradford assay, electrophoresis techniques (e.g., SDS-PAGE, Western blot), etc. For example, the concentration of TIMPs can be determined by testing a sample of amniotic fluid obtained by amniocentesis or at the time of the Caesarean section delivery.

According to embodiments of the invention, a composition used in the methods described herein can further comprise a cryoprotectant. Any cryoprotectant suitable for pharmaceutical use known to those skilled in the art in view of the present disclosure can be used in the composition of the present invention. Examples of cryoprotectants that can be used include, but are not limited to, dimethyl sulfoxide (DMSO), sucrose, glycerol, glucose, and any other sugars, e.g., monosaccharides or disaccharides, alcohols and penetrating agents, or combinations thereof, routinely used as cryoprotectants by those skilled in the art, which will be known to those skilled in the art in view of the present disclosure.

In some embodiments of the invention, the composition is cryopreserved prior to injection into a joint. The cryopreserved composition can be warmed prior to injection to a temperature in a range of about 15° C. to 25° C., such as 15, 16, 17, 18, 19, 20, 21, 22, 23, 24, or 25° C.

In particular embodiments of the invention, the amniotic fluid is a processed amniotic fluid, such as a processed human amniotic fluid. The term "unprocessed," when used with respect to an amniotic fluid, refers to an amniotic fluid that has not been treated, such that it has substantially the same composition, i.e., same components in the same amounts, as the native amniotic fluid found in vivo. The term "processed," when used with respect to an amniotic fluid, means that the amniotic fluid has been treated or manipulated in some way after being collected from the donor, such that it has an altered composition, i.e., same components in different amounts or different components, as compared to the native amniotic fluid found in vivo.

According to embodiments of the invention, a processed amniotic fluid can be prepared from an unprocessed amniotic fluid. For example, a processed amniotic fluid is prepared from an unprocessed amniotic fluid by concentrating the amniotic fluid that is collected from a donor to increase the concentration of TIMPs and/or other components naturally present in the amniotic fluid.

In a preferred embodiment, the processed amniotic fluid is prepared by concentrating an amniotic fluid obtained from a donor by removing at least water to enrich the amniotic fluid for endogenous TIMPs. The amniotic fluid can be further processed such that the substantially all of the endogenous components of the amniotic fluid with the exception of TIMPs are removed from the amniotic fluid. According to embodiments of the invention, a processed amniotic fluid can comprise about 10% to about 100% (w/v) TIMPs, such as, for example, 10%, 20%, 30%, 40%, 50%, 60%, 70%, 80%, 90%, 95%, 99%, or 100% (w/v) TIMPs.

However, the invention is not limited to administering TIMPs as a component of an amniotic fluid, and embodiments of the invention also relate to administering compositions comprising a therapeutically effective amount of TIMPs.

Thus, in yet another general aspect of the invention, a method of treating a joint disease, disorder, or condition in a subject comprises injecting a composition comprising a therapeutically effective amount of tissue inhibitors of matrix metalloproteinases (TIMPs) into the joint of the subject, thereby treating the joint disease, disorder, or condition. The TIMPs can be obtained from an amniotic fluid, or isolated or purified from another natural source. The TIMPs can also be recombinantly produced by any method known in the art. Recombinantly produced TIMPs include, but are not limited to, human recombinant TIMPs.

Embodiments of the invention also relate to harvesting TIMPs from amniotic fluid obtained from the donor, preferably amniotic fluid obtained from the donor at a point during gestation when the level of TIMPs is at or near the maximum. TIMPs harvested from the amniotic fluid can be purified and used to supplement a composition comprising amniotic fluid prior to injection of the composition into a joint. TIMPs harvested from the amniotic fluid can also be purified from the other amniotic fluid components, and the purified TIMPs can be administered in a composition.

According to embodiments of the invention, a composition is injected into a joint. Any of the compositions described herein comprising a therapeutically effective amount of TIMPs can be injected into a joint. Preferably, the composition is injected into a synovial joint, and is more preferably injected into the intra-articular space of a synovial joint. The intra-articular space refers to the space inside of a joint between two bones that is usually contained by the articular capsule. The articular capsule, also referred to as the joint capsule, is the envelope surrounding a synovial joint.

In particularly preferred embodiments, the invention relates to a method of treating osteoarthritis of a synovial joint, comprising injecting a composition comprising an amniotic fluid comprising a therapeutically effective amount of tissue inhibitors of matrix metalloproteinases into the synovial joint. Preferably, the osteoarthritis is associated with degradation of articular cartilage by proteases. According to embodiments of the invention, the synovial joint can be any synovial joint, such as a knee, wrist, shoulder, hip, elbow, or neck joint. In a preferred embodiment, the synovial joint is a knee joint.

Embodiments of the invention also relate to methods of lubricating a joint, such as an osteoarthritic joint, using the compositions described herein, such as a composition comprising an amniotic fluid comprising a therapeutically effective amount of tissue inhibitors of matrix metalloproteinases. Compositions comprising a therapeutically effective amount of TIMPs, such as recombinantly produced TIMPs, or TIMPs purified/isolated from amniotic fluid or another natural source can also be used for joint lubrication. Preferably, the joint to be lubricated is a synovial joint, and is more preferably a knee joint. A method of lubricating a joint according to the invention can be used to provide pain-free joint movement to the subject, facilitate joint movement, and/or prevent bone wear and tear in a joint.

As used herein, an "osteoarthritic joint" refers to a synovial joint affected by osteoarthritis. As used herein, "lubricating a joint" refers to supplementing the amount of synovial fluid present in the joint, or replacing synovial fluid in a joint to increase joint movement and/or prevent bone wear and tear in the joint. Lubricating a joint with a composition comprising a human amniotic fluid comprising a therapeutically effective amount of TIMPs, or a composition comprising a therapeutically effective amount of TIMPs, has the advantage of inhibiting proteases in the joint, thereby also preventing or reducing the breakdown of collagen in the joint while simultaneously replacing or supplementing the synovial fluid in the joint to improve joint movement.

According to embodiments of the invention, a composition used in the treatment of a joint disease, disorder, or condition, or lubrication of a joint, can be used in combination with another treatment including, but not limited to, general exercise; strengthening exercises; walking aids such as canes or crutches; wheeled walkers or frames; knee bracing; orthotics; non-steroidal anti-inflammatory drugs (NSAIDs); thermal treatments including heat therapy; cryotherapy; transcutaneous electrical nerve stimulation; and acupuncture.

According to embodiments of the invention, a composition can be injected into a joint once a day or multiple times a day. The composition can also be injected according to a specified dosing regimen, e.g., once a week for a period of a few weeks or a few months. The dosing regimen can also occur over a period of year. An exemplary and nonlimiting example of a dosing regimen includes one six injections over the course of a year. The optimal frequency and duration of injections of the composition will depend upon various factors including the particular type of joint disease, disorder, or condition to be treated, its underlying cause, whether or not the composition is being used in combination with another treatment (e.g., general exercise or strengthening exercises), etc. For example, in some instances, one injection will be sufficient to provide a clinically beneficial effect. In other instances, more than one injection, such as one injection every two months over the course of the year will be need to realize a clinically beneficial effect. The injection volume can also vary depending upon a variety of factors, such as the particular joint and the size of the joint. For example, a larger injection volume is typically needed for treatment of a joint disease, disorder, or condition when the joint is a knee joint as compared to a finger joint. As general guidance, the injection volume can range from about 0.25 mL to about 6 mL, such as 0.25, 0.5, 0.75, 1.0, 1.5, 2.0, 2.5, 3.0, 3.5, 4.0, 4.5, 5.0, 5.5, or 6.0 mL. One of ordinary skill in the art will be able to determine the frequency and duration of injections of the composition, as well as the appropriate injection volume in view of the above factors in order to achieve the desired outcome.

In another general aspect, the invention provides a composition comprising an amniotic fluid comprising a therapeutically effective amount of tissue inhibitors of matrix metalloproteinases (TIMPs), wherein at least a portion of the TIMPs are exogenously added. The exogenously added TIMPs can be recombinantly produced, and/or isolated or purified from another natural source. The amniotic fluid can also comprises TIMPs that are naturally present in the amniotic fluid. The composition can be used in any of the methods described herein.

Methods of obtaining an amniotic fluid from a donor using the appropriate sterile techniques are well known to those of ordinary skill in the art. One of ordinary skill in the art is also familiar with procedures for safely and humanely obtaining an amniotic fluid from a donor in an aseptic manner. For example, human amniotic fluid can be obtained from a donor who is undergoing an amniocentesis procedure, Caesarean section delivery, or vaginal birth using a specially designed receptacle to collect the fluid. Preferably, the amniotic fluid is obtained from a donor undergoing a Caesarean section delivery, and is more preferably obtained from a donor undergoing a pre-term Caesarean section delivery, i.e., prior to week 37 of gestation Amniotic fluid obtained from a donor undergoing vaginal birth, or from an amniocentesis procedure can also be used with a method of the invention, however a larger quantity of amniotic fluid can be obtained from a donor undergoing a Caesarean section delivery, and is thus the preferred method for obtaining amniotic fluid. Also, amniotic fluid obtained at the time of vaginal delivery at term typically has lower levels of TIMPs.

Preferably, the technique used for harvesting the amniotic fluid should substantially eliminate, or at least minimize, the presence of red blood cells in the amniotic fluid. Furthermore, the amniotic fluid used in the invention should not be cloudy in color, and it should not have any particulate matter. Particulate matter can be removed from the amniotic fluid by any method known in the art for removing particulate matter from biological samples including, but not limited to, filtration and centrifugation. Particulate matter can be removed at any time after the amniotic fluid has been collected. Preferably, the particulate material is removed prior to any other processing or treatment steps.

According to embodiments of the invention, amniotic fluid used in the invention is procured from a female donor. Informed consent is obtained from the female donor by following guidelines as promulgated by the American Association of Tissue Banks and consistent with guidelines provided by the Food and Drug Administration: a federal agency in the Department of Health and Human Services established to regulate the release of new medical products and, finally, if required by an established review body of the participating hospitals or institutions. The female donor is informed that she will be subject to risk assessment to determine if she is qualified as an amniotic fluid donor. She will also be informed of the tests for the risk assessment. The female donor is further informed that, if she is selected as an amniotic fluid donor based on the risk assessment, her birth tissues, such as placenta and amniotic fluid, may be collected at birth, tested and processed for medical uses. The informed consent includes consent for risk assessment and consent for donation of birth tissues and amniotic fluid.

Risk assessment is conducted on the female donor with informed consent to evaluate her risk factors for communicable diseases, such as human immunodeficiency virus (HIV), hepatitis B virus (HBV), hepatitis C virus (HCV), cytomegalovirus (CMV), human T-lymphotropic virus (HTLV), syphilis, etc., as is required by regulating bodies. Medical and social histories of the female donor, including physical exam record, and/or risk assessment questionnaire, are reviewed. Those with high risk factors for the communicable diseases are excluded.

Consent to draw blood at the time of delivery and 1 to 12 months post-delivery is obtained from female donors with low risk factors for the communicable diseases. Screening tests on communicable diseases, such as HIV 1 and 2, HCV, HbCore, syphilis, HTLV I/II, CMV, hepatitis B and C, are conducted by conventional serological tests on the blood sample obtained at birth. The initial screening tests are preferably completed within 7 days after birth. Preferably, the screening tests are conducted again on a second blood sample collected a few months post-delivery, to verify the previous screening results and to allow for detection of communicable disease acquired shortly before birth, but are shown as "negative" on the previous screening tests. The second blood sample can be collected 1-12 months, preferably 6 months, post birth.

Only female donors with informed consent who are tested negative for the communicable diseases are approved as amniotic fluid donors. In a preferred embodiment, only female donors with informed consent who are tested negative for the communicable diseases in both screening tests with the blood sample drawn at birth and the blood sample drawn 6 months post-delivery are approved as amniotic fluid donors.

According to embodiments of the invention, the amniotic fluid can be treated in such a way as to promote preservation, lengthen shelf life, etc. These treatments include, but are not limited to, sterilization, e.g., gamma-irradiation; cooling, refrigeration, and freezing; and addition of one or more preservatives, cryopreservatives, antimicrobial agents, etc.

According to embodiments of the invention, once collected from the donor, the amniotic fluid can be processed to provide a processed amniotic fluid. Thus, in particular embodiments of the invention, an amniotic fluid of a composition used in a method of the invention is a processed amniotic fluid.

In one embodiment, the amniotic fluid is processed to remove water, and optionally other components from the amniotic fluid. For example, using an ultrafiltration approach, a semi-permeable container is filled with raw amniotic fluid, and then a pressure gradient is applied across the semi-permeable membrane using any number of techniques known to those skilled in the art including, but not limited to, a high permeability dialyzer. As another illustrative example, when employing hemodialysis techniques, an electrolyte solution (dialysate) can be applied on one side of a membrane, creating a concentration gradient, which causes water and other non-protein cellular components of the amniotic fluid to flow through the semi-permeable membrane. As yet another illustrative example, rapid ultrafiltration approaches can be used. Rapid ultrafiltration approaches employ a semi-permeable membrane cylindrical container that rotates constantly in order to avoid filter clogging even as a pressure gradient is applied to the contained fluid-either from within the container (pushing), or from the opposite side of the semi-permeable membrane (pulling).

A processed amniotic fluid can be prepared by removing water from the amniotic fluid obtained from a donor by any technique known to those of ordinary skill in the art to provide a processed amniotic fluid. For example, substantially all of the water can be removed by lyophilization, etc., or the amount of water can be reduced by vacuum filtration, etc.

A processed amniotic fluid can also be prepared from an unprocessed amniotic fluid by increasing the concentration of one or more of proteins, carbohydrates, lipids, and other desirable components in the amniotic fluid using any technique known to those of ordinary skill in the art in view of the present disclosure. For example, a desirable endogenous component, e.g., TIMPs, can be enriched by filtration or centrifugation with specific parameters. An exogenous desirable component can also be added to the processed amniotic fluid.

In another embodiment, a processed amniotic fluid has a different viscosity as compared to the unprocessed amniotic fluid. The amniotic fluid can be further processed so that it has a relatively high viscosity for ease of application and for remaining in the desired area after the application. For example, the amniotic fluid can be concentrated to remove water by centrifugation, lyophilization, vacuum filtration, etc., which will also concentrate many of the other amniotic fluid components, such as TIMPs, thus increasing their concentration. Increasing the concentration of TIMPs and/or other components in the amniotic fluid can achieve optimal therapeutic concentrations of TIMPs, as well as other amniotic fluid components, which can further enhance treatment of the joint disease, disorder, or condition.

In one embodiment, a processed amniotic fluid has one or more different components, such as proteins, lipids, and carbohydrates, as compared to the unprocessed amniotic fluid.

In another embodiment, a processed amniotic fluid has the same components, such as proteins (e.g., TIMPs), lipids, and carbohydrates, as compared to the unprocessed amniotic fluid, but the components are present in different amounts, i.e., in an increased concentration or a decreased concentration.

For example, a processed amniotic fluid comprising a therapeutically effective amount of TIMPs can be an amniotic fluid supplemented with exogenous TIMPs. Supplementing the amniotic fluid collected from the female donor with exogenous TIMPs, e.g., purified TIMPs or recombinantly produced TIMPs, can increase the effective concentration of TIMPs in the amniotic fluid and further enhance its effects on treating joint diseases, disorders, and conditions.

In another embodiment, a processed amniotic fluid is prepared from an unprocessed amniotic fluid by removing non-protein nitrogenous compounds, such as uric acid, urea, creatinine, and nitrogen from the amniotic fluid. These non-protein nitrogenous compounds can be removed by any method known in the art, such as by means of a semipermeable membrane or filter, or by dialysis. Other suitable means for removing these compounds include osmotic, centrifugal, gravitational or mechanical pumping forces.

According to embodiments of the invention, the concentrations of the components found in the unprocessed amniotic fluid, particularly inorganic constituents, gases, non-protein nitrogenous compounds, proteins, carbohydrates, and lipids, differ from the concentrations found in the processed amniotic fluid. The concentration of any one particular component in the processed amniotic fluid can be increased, decreased, or unchanged as compared to the concentration in the unprocessed amniotic fluid, independent of any other component. For example, the concentration of creatinine in the processed amniotic fluid can be decreased, whereas the concentration of glucose can be increased, as compared to their respective concentrations in the unprocessed amniotic fluid.

According to embodiments of the invention, a processed amniotic fluid can comprise an increased concentration of at least one of a first component selected from the group consisting of proteins, lipids, and carbohydrates as compared to a concentration in an unprocessed amniotic fluid; and a decreased concentration of at least one of a second component selected from the group consisting of urea, uric acid, and creatinine, as compared to a concentration in the unprocessed amniotic fluid.

In one particular embodiment a composition used in a method of the invention comprises a processed amniotic fluid having increased concentrations of proteins as compared to the unprocessed amniotic fluid. According to this embodiment, the total protein concentration can be increased in the processed amniotic fluid, such that the aggregate protein content ranges from about 30.25 g/L to about 50.375 g/L. The concentrations of at least one of cytokines, such as interleukin (IL)-6, IL-8, IL-β, and tumor necrosis factor (TNF)-a, can be increased in the processed amniotic fluid; and the concentrations of at least one of globulins, such as a-globulins, β-globulins, and γ-globulins, can be increased as compared to their concentrations in the unprocessed amniotic fluid. According to other embodiments of the invention, albumin comprises no less than 60% of the total protein content in the processed amniotic fluid. The concentration of other proteins present in the unprocessed amniotic fluid, such as C-reactive protein, procalcitonin, and/or calprotecin can be present in the processed amniotic fluid, or they can be eliminated.

In preferred embodiments of the invention, in the processed amniotic fluid, the concentration of a-globulins is at least 12% of the total protein concentration, preferably 12% to 18%; the concentration of β-globulins is at least 16% of the total protein concentration, preferably 16% to 27%; and the concentration of γ-globulins is at least 12% of the total protein concentration, preferably 12% to 18%. In other preferred embodiments, in the processed amniotic fluid, the concentration of IL-6 is at least 329 ng/L, the concentration of IL-8 is at least 421 ng/L, the concentration of IL-1β is at least 3.9 ng/L and the concentration of TNF-a is at least 11.5 ng/L.

In another particular embodiment, a composition used in a method of the invention comprises a processed amniotic fluid having increased concentrations of lipids as compared to the unprocessed amniotic fluid. According to this embodiment, the concentrations of at least one of fatty acids, cholesterol, and phospholipids in the processed amniotic fluid are increased as compared to their respective concentrations in the unprocessed amniotic fluid. The processed amniotic fluid can comprise fatty acids at a concentration of about 0.25 g/L to about 6.5 g/L; cholesterol at a concentration of about 0.5 g/L to about 9.5 g/L; and/or phospholipids at a concentration of about 0.003 g/L to about 0.3 g/L.

In yet another particular embodiment, a composition used in a method of the invention comprises a processed amniotic fluid having increased concentrations of carbohydrates as compared to the unprocessed amniotic fluid. In this embodiment, the concentration of one or more of glucose, fructose, hyaluronic acid, and lubricin in the processed amniotic fluid is increased as compared to their respective concentrations in the unprocessed amniotic fluid. Lubricin (proteoglycan 4) is a proteoglycan present in synovial fluid that acts as lubricant. These carbohydrates function to provide lubrication, protection and shock absorption, particularly to inflamed joints. The processed amniotic fluid can comprise glucose at a concentration of about 600 mg/L to about 900 mg/L; fructose at a concentration of about 48 mg/L to about 59 mg/L; hyaluronic acid at a concentration of about 30 μg/L to about 3600 μg/L; and/or lubricin at a concentration of about 10 μg/ml to about 200 μg/ml.

And in yet another particular embodiment, a composition used in the method of the invention comprises a processed amniotic fluid having decreased concentrations of non-protein nitrogenous compounds as compared to the unprocessed amniotic fluid. For example, the concentrations of one or more of urea, uric acid, and creatinine in the processed amniotic fluid are decreased as compared to their respective concentrations in the unprocessed amniotic fluid. Preferably, the concentration of urea is no more than 160 mg/L, the concentration of uric acid is no more than 80 g/L, and/or the concentration of creatinine is no more than 14 mg/Lin the processed amniotic fluid of a composition used with the invention.

According to embodiments of the present invention, the pH of a composition ranges from a pH of about 6.0 to a pH of about 8.0, such as 6.0, 6.5, 7.0, 7.5, or 8.0. Preferably, the pH ranges from 6.5 to 7.5, and is more preferably 7.0.

In other particular embodiments, compositions used in the methods of invention comprise a processed amniotic fluid having optimized concentrations of inorganic constituents and optimized partial pressures of gases, such that the concentrations and partial pressures closely approximate the concentrations of these components in the native synovial fluid. Such inorganic constituents include sodium, potassium, and chloride, and such gases include oxygen and carbon dioxide.

Other examples of processed amniotic fluids suitable for use in the invention, and processes for preparing such processed amniotic fluids are described in U.S. patent application Ser. No. 14/950,186, which is herein incorporated by reference in its entirety.

The compositions used in the invention can further comprise additional substances including pharmaceutically acceptable excipients, such as thickeners, salts, preservatives, colorants, etc.; substances to prevent the growth of microbes, such as antifungal, antibacterial, or antiviral agents; and agents that improve the viscosity or thickness of the composition. These additions can be made, provided that they do not cause irritation of the joint, or interfere with the healing properties of the amniotic fluid. The compositions of the present invention can also further comprise one or more pharmaceutically active ingredients, such as an analgesic, an anti-inflammatory agent, an anti-microbial agent, etc.

An illustrative and non-limiting example of an embodiment of a composition comprising a processed amniotic fluid that can be used in a method of the invention is shown in Table 1 below. According to embodiments of the invention, the processed amniotic fluid further comprises a therapeutically effective amount of tissue inhibitors of matrix metalloproteinases.

TABLE 1

Concentrations of inorganic constituents, gases, proteins, carbohydrates, lipids, and non-protein nitrogenous compounds in an embodiment of an amniotic fluid of a composition used in a method of the invention.

| Component | Unprocessed Amniotic fluid[1] | Composition Target Ranges post-processing | | Discussion and Function |
|---|---|---|---|---|
| | | High | Low | |
| Inorganic Constituents | | | | |
| Sodium | 127 mEq/L | 148.375 | 85.625 | Stay within prescribed range |
| Potassium | 4.0 mEq/L | 48.125 | 21.875 | Increase from about 4.0 mEq/L in source material to a minimum of 21.875 mEq/L |
| Chloride | 105 mEq/L | 145.75 | 66.25 | Stay within prescribed range |
| Calcium | 4.0 mEq/L | 7.21875 | 3.28125 | Stay within prescribed range |
| Magnesium | 1.4 mEq/L | 2.75 | 1.25 | Stay within prescribe range |
| Phosphorus | 29.0 mg/L | 55 | 22 | |
| Gases/H+ | | | | |
| pH | 7.0 | 7.9375 | 6.125 | In order to restore the proper acid/base balance in an acidic and arthritic joint, stay within the prescribed range |
| PO2 | 2-15 mm Hg | 78 | 8 | In order to provide the proper oxygenation range for use as a viscosuppplement in an arthritic joint, increase the two prescribed ranges |
| PCO2 | 57 mm Hg | 150 | 34 | |
| Protein (Total) | 22-31 g/L | 50.375 | 30.25 | Increase the amount of protein to the prescribed range |
| Albumin | 60% | | 60% | Ensure that Albumin comprises no less than 60% of the protein content |
| α-globulins | 12% | 18% | 12% | Stay within prescribed range |
| B-globulins | 16% | 27% | 16% | Stay within prescribed range |
| γ-globulins | 12% | 18% | 12% | Stay within prescribed range |
| Cytokines | | | | |
| IL-6 | 329 ng/L | | 329 ng/L | No less than the prescribed amount |
| Il-8 | 421 ng/L | | 421 ng/L | No less than the prescribed amount |
| IL-1β | 3.9 ng/L | | 3.9 ng/L | No less than the prescribed amount |
| TNF-α | 11.5 ng/L | | 11.5 ng/L | No less than the prescribed amount |
| C-reactive protein (CRP) | 5.4 mg/L | | | May be present or may be eliminated in any embodiment of the invention |
| Procalcitonin | 1.8 μg/L | | | May be present or may be eliminated in any embodiment of the invention |
| Calprotecin | 3425 μg/L | | | May be present or may be eliminated in any embodiment of the invention |

TABLE 1-continued

Concentrations of inorganic constituents, gases, proteins, carbohydrates, lipids, and non-protein nitrogenous compounds in an embodiment of an amniotic fluid of a composition used in a method of the invention.

| Component | Unprocessed Amniotic fluid[1] | Composition Target Ranges post-processing | | Discussion and Function |
|---|---|---|---|---|
| | | High | Low | |
| Non-Protein Nitrogen Compounds | | | | These by-products of metabolism are reduces in the final viscosupplment fluid |
| Urea | 370 mg/L | 160 | 82.5 | Reduce quantities such that the amounts are no more than the maximum amount prescribed |
| Uric Acid | 50 mg/L | 80 | 22.5 | Reduce quantities such that the amount are no more than the maximum amount prescribed |
| Creatinine | 28 mg/L | 14 | 8.75 | Reduce quantities such that the amounts are no more than the maximum amount prescribed |
| Carbohydrates | | | | These carbohydrates are important to supply proper levels of nutrients, lubrication, compression and shear resistance and cushioning to the living musculoskeletal joint |
| Glucose | 330 mg/L | 900 | 600 | Increase quantity to the prescribed ranges |
| Fructose | 35 mg/L | 58.625 | 48.125 | Increase quantity to the prescribed ranges |
| Lactic Acid | 370-750 mg/L | 250 | 156.25 | Reduce quantities such that the amounts are no more than the maximum amount prescribed |
| Pyruvate | 8 mg/L | 13.4 | 11 | Increase quantity to the prescribed range |
| Hyaluronan: mean (SD) | 22.67(10.8)/ 1.1(0.46) μg/L | 3600 μg/ml | 30 μg/L | Provides Compression & Shear Resistance and is a carrier for surface active phospholipids (SAPL), which are boundary lubricant in viscosupplement fluids. Increase to levels within the prescribed levels |
| Lubricin (PRG4) | | 200 μg/ml | 10 μg/ml | This is a protein which is related to MCF and is likely carrier for SAPL. Increase to the prescribed levels |
| Total Lipids | 0.48 g/L | | | |
| Fatty Acids | 0.24 g/L | 6.50 g/L | 0.25 g/L | Increase quantity to the prescribed ranges |
| Cholesterol | 0.02 g/L | 9.50 g/L | 0.50 g/L | Increase quantity to the prescribed ranges |
| Phospholipids (Total) | 0.03 g/L | .030 mg/ml | 0.003 g/L | Increase quantity to the prescribed ranges |

[1]References (24)-(33) were used to determine the quantities of the components in the unprocessed amniotic fluid Any of the processed amniotic fluids described herein can be used in any of the methods of the invention including methods of treating joint diseases, disorders, and conditions, methods of treating osteoarthritis in a synovial joint, methods of treating osteoarthritis associated with degradation of articular cartilage by proteases, methods of lubricating a joint, such as an osteoarthritic joint, etc.

Proteases, particularly matrix metalloproteinases (MMPs), are known to degrade the collagen. With respect to joints, MMPs can degrade collagen in the articular cartilage, which causes the cartilage to wear down, leading to various joint conditions including, but not limited to osteoarthritis. Without wishing to be bound by any theories, it is believed that TIMPs can inhibit the activity of proteases in joints, particularly MMPs, thereby alleviating joint conditions such as osteoarthritis. Again without wishing to be bound by any theories, it is further believed that TIMPs naturally present in amniotic fluid can inhibit the activity of proteases in joints, thereby alleviating joint conditions such as osteoarthritis. Moreover, compositions comprising amniotic fluid are thought to more closely approximate the composition of synovial fluid as compared to conventional viscosupplements and other injection materials used to treat joint diseases, disorders, and conditions, and are thus believed to better provide not only the requisite lubrication, cushioning, and protection of the joint, but also the components and pH level required for maintaining the healthy biological and physiological function of the entire joint system.

EXAMPLE

Example 1: Treatment of Knee Osteoarthritis

A patient experiencing knee pain is diagnosed with knee osteoarthritis. The patient is administered a composition comprising a therapeutically effective amount of TIMPs by injection directly into the synovial joint. The composition contains amniotic fluid that was harvested from an elective Caesarean section birth during week 37 of pregnancy. Pain relief is monitored using the Visual Analog Scale (VAS) and Western Ontario and McMaster Universities Arthritis Index (WOMAC) methods. The composition is administered one or more times after the initial injection, as needed, to further relieve pain.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES (1) Trelford et al. The amnion in surgery, past and present. *Am J Obstet Gynecol*. (1979) 134(7): 833-45.
(2) Niknejad et al. Properties of the amniotic membrane for potential use in tissue engineering. *Eur Cell Mater*. (2008) 15, 88-99.
(3) Weiss et al. The matrix metalloproteinases (MMPs) in the decidua and fetal membranes. *Frontiers in Bioscience* (2007) 12, 649-59.
(4) Riley et al. Secretion of tissue inhibitors of matrix metalloproteinases by human fetal membranes, decidua, and placenta at parturition. *J Endocrinology* (1999) 162, 351-59.
(5) Maymon et al. A role for the 72 kDa gelatinase (MMP-2) and its inhibitor (TIMP-2) in human parturition, premature rupture of membranes and intraamniotic infection. *J Perinatal Medicine* (2005) 29(4), 308-316.
(6) Athayde et al. Matrix metalloproteinases-9 in preterm and term human parturition. *J Matern. Fetal Med* (1999) 8(5), 213-9.
(7) Menon et al. The role of matrix degrading enzymes and apoptosis in rupture of membranes. *J Soc. Gynecol. Investig.* (2004) 11(7), 427-37.
(8) McLaren et al. Increased concentration of pro-matrix metalloproteinase 9 in term fetal membranes overlying the cervix before labor: implications for membrane remodeling and rupture.
(9) Athayade et al. A role for matrix metalloproteinase-9 in spontaneous rupture of the fetal membranes. *Am. J Obstet. Gynecol.* (1998) 179(5), 1248-53.
(10) Pasquier et al. Fetal membranes: embryological development, structure and the physiopathology of the preterm premature rupture of membranes. *J Gynecol. Obstet. Biol. Reprod (Paris)* (2008) 37(6), 579-88.
(11) Moore et al. The physiology of fetal membrane rupture: insight gained from the determination of physical properties. *Placenta* (2006) 27(11-12) 1037-51.
(12) Park et al. Role of cytokines in preterm labor and birth. *Minerva Ginecol.* (2005) 57(4), 349-66.
(13) Wang et al. Role of matrix metalloproteinases-2,9 and their inhibitors in premature rupture of membranes. *Zhonghua Fu Chan Ke Za Zhi* (2005) 40(1) 29-33.
(14) Lu et al. Clinical significance of matrix metalloproteinase-9/tissue inhibitors of matrix metalloproteinase-1 imbalance in maternal serum, amniotic fluid, umbilical cord serum in patients with premature rupture of the membranes.
(15) Vadillo-Ortega et al. 92-kd type IV collagenase (matrix metalloproteinase-9) activity in human amniochorion increases with labor. *Am. J Pathol.* (1995) 146(1), 148-56.
(16) Gordon et al. Metalloproteinase inhibitors as therapeutics. *Clin. Exp. Rheumatol.* (1993) Suppl. 8: S91-4.
(17) Fortunato et al. Presence of four tissue inhibitors of matrix metalloproteinases (TIMP-1, -2, -3, and -4) in human fetal membranes. *Am. J Reprod Immunol.* (1998) 40(6), 395-400.
(18) Fortunato et al. Collagenolytic enzymes (gelatinases) and their inhibitors in human amniochorionic membrane. *Am. J Obstet. Gynecol.* (1997) 177(4), 731-41.
(19) Vadillo-Ortego et al. Increased matrix metalloproteinase activity and reduced tissue inhibitor of metalloproteinases-1 levels in amniotic fluids from pregnancies complicated by premature rupture of membranes. *Am. J Obstet. Gynecol.* (1996) 174(4), 1371.
(20) Hampson et al. Amniotic membrane collagen content and type distribution in women with preterm premature rupture of the membranes in pregnancy. *Br. J Obstet. Gynecol.* (1997) 104(9), 1087.
(21) Bryant-Greenwood et al. Control of peripartal collagenolysis in the human chorion-decidua. *Am. J Obstet. Gynecol.* (1995) 172 (1 Pt 1): 63.
(22) Draper et al. Elevated protease activities in human amnion and chorion correlate with preterm premature rupture of membranes. *Am. J Obstet. Gynecol.* (1995) 173(5) 1506.
(23) Lei et al. 92 kDa gelatinase (matrix metalloproteinase-9) is induced in rat amnion immediately prior to parturition. *Biol. Reprod* (1995) 53(2): 339.
(24) Assali N A: Biology of Gestation, Vol 1, p 276, New York, Academic Press, 1968.
(25) Engstrom-Laurent A and T C Laurent. Clinical Impact of Bone and Connective Tissue Markers Pg 237 Academic Press 1989 (AF values are for 16 weeks and 39 weeks gestation, respectively).
(26) Laurent U B G, R K Reed. *Advance Drug Delivery Reviews* 7:237-256 (1991).
(27) Cajori A F. *J Biol Chem.* 76:471-480 (1928).
(28) Treuhaft P S and D J McCarty *Arthritis & Rheumatism* 14(4):475-484 (1971).
(29) Osteoarthritis: Diagnosis and Medical/Surgical Management (Moskowitz ed.), pg 207 Lippincott Williams & Wilkins (2007).
(30) Bole G G. *Arthritis and Rheumatism* 5(6):589-601 (1962).
(31) Wilson S E et al. IOVS 30(3):449-453 (1989).
(32) Cenedella R J. *Biochimica et Biophysic Acta* 793:448-454 (1984).
(33) Schmidt T A et al. *JAMA Ophthalmol* 131(6):766-776 (2013).
(34) Murphy et al. Lifetime risk of symptomatic knee osteoarthritis. *Arthritis Rheum.* 2008; 59(9): 1207-1213
(35) Murphy et al. One in four people may develop symptomatic hip osteoarthritis in his or her lifetime. *Osteoarthritis Cartilage* 2010; 18(11):1372-9.

We claim:

1. A method of treating a joint disease, disorder, or condition in a subject in need thereof, the method comprising injecting a composition comprising an enriched amniotic fluid comprising a therapeutically effective amount of tissue inhibitors of matrix metalloproteinases (TIMPs) into the joint of the subject, thereby treating the joint disease, disorder, or condition, wherein particulate matter in an amniotic fluid is substantially eliminated in the amniotic fluid prior to the composition being injected into the joint and the amniotic fluid is enriched for endogenous TIMPs whereby the enriched amniotic fluid includes the therapeutically effective amount of the TIMPs.

2. The method according to claim 1, wherein the joint is selected from the group consisting of a synovial joint and a cartilaginous joint.

3. The method according to claim 1, wherein the joint disease, disorder, or condition is associated with degradation of cartilage by proteases.

4. The method according to claim 3, wherein the proteases comprise matrix metalloproteinases.

5. The method according to claim 1, wherein the joint disease, disorder, or condition is selected from the group consisting of joint inflammation, osteoarthritis, rheumatoid arthritis, and chondromalacia patellae.

6. The method according to claim 1, wherein the joint is a synovial joint.

7. The method according to claim 1, wherein the joint is a knee joint.

8. The method according to claim 1, wherein the amniotic fluid is obtained from a pregnant female donor during a Caesarean section procedure.

9. The method according to claim 1, including determining that the amniotic fluid does not contain a therapeutically effective amount of the TIMPs and removing water from the amniotic fluid to enrich the amniotic fluid for endogenous TIMPs.

10. The method according to claim 1, wherein the joint disease, disorder, or condition is osteoarthritis of a synovial joint, wherein the osteoarthritis is associated with degradation of articular cartilage by proteases, and the composition is injected into the synovial joint.

11. The method according to claim 10, wherein the proteases are matrix metalloproteinases.

12. The method according to claim 10, wherein the synovial joint is a knee joint, wrist joint, shoulder joint, hip joint, elbow joint, or neck joint.

13. The method according to claim 12, wherein the synovial joint is a knee joint.

14. The method according to claim 1, including determining that the amniotic fluid does not contain a therapeutically effective amount of the TIMPs and increasing the TIMPs concentration in the amniotic fluid whereby the enriched amniotic fluid includes the therapeutically effective amount of the TIMPs.

15. The method according to claim 1, wherein the amniotic fluid is processed by removing water to enrich the amniotic fluid for endogenous TIMPs thereby providing a processed amniotic fluid having a TIMPs concentration selected from the group consisting of 10% w/v, 20% w/v, 30% w/v, 40% w/v, 50% w/v, 60% w/v, 70% w/v, 80% w/v, 90% w/v, 95% w/v and 99% w/v.

16. A method of lubricating an osteoarthritic joint in a subject in need thereof, wherein the osteoarthritis of the joint is associated with degradation of articular cartilage by proteases, the method comprising injecting into the joint a composition including an enriched amniotic fluid comprising a therapeutically effective amount of tissue inhibitors of matrix metalloproteinases, thereby lubricating the osteoarthritic joint, wherein particulate matter in an amniotic fluid is substantially eliminated in the amniotic fluid prior to the composition being injected into the joint and the amniotic fluid is enriched for endogenous TIMPs whereby the enriched amniotic fluid includes the therapeutically effective amount of the TIMPs.

17. The method according to claim 16, wherein the subject is in need of joint lubrication to provide pain-free joint movement.

18. A method of treating a joint disease, disorder, or condition in a subject in need thereof, the method comprising injecting a composition including an enriched amniotic fluid comprising a therapeutically effective amount of tissue inhibitors of matrix metalloproteinases (TIMPs) into the joint of the subject, thereby treating the joint disease, disorder, or condition, wherein particulate matter in an amniotic fluid is minimized and the amniotic fluid is enriched for endogenous TIMPs whereby the enriched amniotic fluid includes the therapeutically effective amount of the TIMPs.

19. The method according to claim 18, wherein the joint is a synovial joint and the joint disease, disorder, or condition is osteoarthritis.

20. The method according to claim 18, including adding recombinantly produced TIMPs to the amniotic fluid.

* * * * *